US 6,679,841 B2

(12) United States Patent
Bojan et al.

(10) Patent No.: US 6,679,841 B2
(45) Date of Patent: Jan. 20, 2004

(54) FLUID COLLECTION AND MONITORING DEVICE

(75) Inventors: Peter M. Bojan, Grayslake, IL (US); Timothy P. Henning, Vernon Hills, IL (US); Neil W. Loomis, Racine, WI (US); Mark R. Pope, Grayslake, IL (US); Jonathan A. Eppstein, Atlanta, GA (US)

(73) Assignee: Abbott Laboratories, Abbott Park, IL (US)

( * ) Notice: Subject to any disclaimer, the term of this patent is extended or adjusted under 35 U.S.C. 154(b) by 94 days.

(21) Appl. No.: 09/880,948

(22) Filed: Jun. 15, 2001

(65) Prior Publication Data

US 2002/0099308 A1 Jul. 25, 2002

(Under 37 CFR 1.47)

Related U.S. Application Data

(63) Continuation of application No. 09/250,701, filed on Feb. 16, 1999, now abandoned.
(60) Provisional application No. 60/074,866, filed on Feb. 17, 1998.

(51) Int. Cl.[7] .................................................. A61B 5/00
(52) U.S. Cl. ..................... 600/309; 600/310; 600/345; 600/584
(58) Field of Search .................................. 600/309, 310, 600/344, 345, 348, 362, 573, 584; 422/68.1, 82.01, 82.05; 204/403.01, 403.02

(56) References Cited

U.S. PATENT DOCUMENTS 4,545,382 A    10/1985   Higgins et al.

(List continued on next page.)

FOREIGN PATENT DOCUMENTS

WO            9409713         5/1994

*Primary Examiner*—Eric F. Winakur
(74) *Attorney, Agent, or Firm*—David L. Weinstein

(57) ABSTRACT

An article capable of both collecting interstitial fluid and detecting an analyte in that fluid and a method for use of that article. Preferably, the article is also capable of measuring the amount of analyte in the interstitial fluid. The article can be used in conjunction with a meter that contains an appropriate detection element for determining the amount of analyte in the interstitial fluid. In one preferred embodiment, the article is a multiple-layer element comprising:

(1) a layer that is capable of being placed in contact with the skin of a patient;
(2) a layer that is coated over the skin-contacting layer;
(3) a layer, substantially coplanar with the overcoat layer, that is capable of transporting interstitial fluid by means of chemically aided wicking;
(4) a layer, overlying the interstitial fluid transporting layer, that is capable of being placed in contact with a meter, said layer having an opening therein through which light can be transmitted;
(5) a layer, disposed on the surface of the meter-contacting layer that faces the skin-contyacting layer, that is capable of detecting the presence of analyte or measuring the amount of analyte in the fluid.

In order to use the multiple-layer element, light from a source of light is transmitted through the opening in the multiple-layer material to be absorbed at a light-absorbing target on the skin-contacting layer. This light transfers energy to the target, and this transferred energy causes an opening to form in the skin-contacting layer and an opening to form in the stratum corneum. Interstitial fluid exudes from the opening in the stratum corneum and contacts the interstitial fluid transporting layer. The interstitial fluid then moves along or through the interstitial fluid transporting layer to the detecting layer.

32 Claims, 7 Drawing Sheets

U.S. PATENT DOCUMENTS

| | | |
|---|---|---|
| 4,653,513 A | 3/1987 | Dombrowski |
| 4,711,245 A | 12/1987 | Higgins et al. |
| 4,775,361 A | 10/1988 | Jacques et al. |
| 4,929,545 A | 5/1990 | Freitag |
| 4,935,346 A | 6/1990 | Phillips et al. |
| 5,076,273 A * | 12/1991 | Schoendorfer et al. ..... 600/584 |
| 5,140,985 A * | 8/1992 | Schroeder et al. .......... 600/323 |
| 5,165,418 A | 11/1992 | Tankovich |
| 5,374,556 A | 12/1994 | Bennett et al. |
| 5,423,803 A | 6/1995 | Tankovich et al. |
| 5,582,184 A * | 12/1996 | Erickson et al. ............ 600/584 |
| 5,628,890 A * | 5/1997 | Carter et al. ................ 600/347 |
| 5,676,144 A * | 10/1997 | Schoendorfer .............. 600/584 |
| 5,682,884 A | 11/1997 | Hill et al. |
| 6,219,574 B1 * | 4/2001 | Cormier et al. ............. 600/362 |

\* cited by examiner

FLUID COLLECTION AND MONITORING DEVICE

This application is a continuation of Ser. No. 09/250,701 filed Feb. 16, 1999 now abandoned, which claims benefit of Provisional No. 60/074,866 filed Feb. 17, 1998.

BACKGROUND OF THE INVENTION

1. Field of the Invention

This invention relates to a method and apparatus for collecting interstitial fluid and analyzing same for the presence of an analyte. More particularly, the analyte is glucose.

2. Discussion of the Art

The prevalence of diabetes has been increasing markedly in the world. At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lance. An individual then coats a paper strip carrying chemistry with the blood, and finally insert the blood-coated strip into a blood glucose meter for measurement of glucose concentration by determination of change in reflectance.

The medical apparatus of the prior art for monitoring the level of glucose in the blood stream required that an individual have separately available a needle or lancet for extracting blood from the individual, strips carrying blood chemistry for creating a chemical reaction with respect to the glucose in the blood stream and changing color, and a blood glucose meter for reading the change in color indicating the level of glucose in the blood stream. The level of blood glucose, when measured by a glucose meter, is read from a strip carrying the blood chemistry through the well-known process of reading reflectometers for glucose oxidation.

Generally lancets comprise a blade and a pressable end opposed thereto, with the blade having an acute end capable of being thrust into skin of a human. By striking the pressable portion, the acute end of the blade will pierce the skin, for example, of the finger. The finger lancet is primarily used to obtain small volumes of blood, i.e., less than 1 mL. Diabetics use the finger lancet to obtain volumes of blood less than 25 $\mu$L for analysis for glucose. A small amount of blood for the blood test will ooze out of the skin. There are many small blood vessels in each finger so that a finger can be squeezed to cause a larger drop of blood to ooze. The finger is one of the most sensitive parts of the body; accordingly, the finger lancet leads to even more pain than what would be experienced by extracting blood via lancet at a different body site. The finger lancet presents another problem because of the limited area available on the fingers for lancing. Because diabetics typically monitor their blood glucose levels two to four times per day, the limited area on the fingers calls for repeated lancing of areas that are already sore. Because fingers are sensitive to pain, it is a recent tendency that the arm is subjected to blood sampling. See, for example, U.S. Pat. No. 4,653,513. The device of U.S. Pat. No. 4,653,513 comprises a cylindrical housing and a lancet support, which has a gasket or flexible portion slidably accommodated in the housing. Springs will retract the lancet support to thereby reduce air pressure in the housing so that it sucks a blood sample, automatically and immediately after a lancet pierces the skin.

Because the blood volume requirements for a standard glucose test strip is typically 3 $\mu$L or more, an area of the body that can generate that much blood from a lancet wound must be used. It is believed, however, that improvements in glucose test strip technology will reduce the volume of blood needed to 1 to 3 $\mu$L. Because the finger is well supplied with blood and the amount of blood can be increased by squeezing the finger after lancing, the finger is the currently preferred body site for lancing, even though lancing of the finger is painful.

A less painful technique for obtaining body fluids could be found if a reliable method were found for lancing a body part that is less sensitive to pain than the finger and obtaining a useful amount of blood from that body part. A body part such as the forearm is much less sensitive to pain than the finger, but the amount of blood resulting from the lancing procedure is generally of an inadequate volume for use with current detection technology. Ways of increasing blood flow to the finger are common knowledge. The recommendation is made to diabetics to run their finger under hot water prior to lancing to improve the blood flow in the finger and the amount of blood collected from the lancet. Running hot water over a body part to improve blood flow is impractical for areas such as the forearm or thigh. The availability of hot water is also a concern. It would be desirable to develop a technique and apparatus for obtaining blood for diagnostic purposes in a painless, reliable manner.

Several patents have proposed that the level of glucose in blood can be monitored by measuring the level of glucose in interstitial fluid. In order to obtain samples of interstitial fluid, the barrier function of the stratum corneum must be overcome. Jacques, U.S. Pat. No. 4,775,361, discloses a method of ablating the stratum corneum of a region of the skin of a patient by using pulsed laser light of a wavelength, pulse length, pulse energy, pulse number, and pulse repetition rate sufficient to ablate the stratum corneum without significantly damaging the underlying epidermis. This patent discloses the use of laser light having a wavelength of 193 nm or 2940 nm. Laser light having wavelengths of 193 nm or 2940 nm can be provided by an excimer or Er:YAG light source, respectively, both of which are extremely expensive.

Tankovich, U.S. Pat. No. 5,423,803, discloses a process for the removal of superficial epidermal skin cells, i.e., stratum corneum, in the human skin. A contaminant having a high absorption in at least one wavelength of light is topically applied to the surface of the skin. Some of the contaminant is forced to infiltrate into spaces between superficial epidermal cells. The skin section is illuminated with short laser pulses at the above wave-length, with at least one of the pulses having sufficient energy to cause some of the particles to explode tearing off the superficial epidermal cells. In a preferred embodiment, the contaminant includes 1 micron graphite particles and the laser used is a Nd:YAG laser.

Zahrov, WO 94/09713, discloses a method for perforating skin comprising the steps of (a) focusing a laser beam in the shape of an ellipse at the surface of the skin with sufficient energy density to create a hole at least as deep as the keratin layer and at most as deep as the capillary layer; and (b) creating at least one hole, each hole having a width between 0.05 and 0.5 mm and a length of equal to or less than 2.5 mm. This patent discloses a variety of lasers suitable for carrying out this method. However, the method disclosed in Zahrov is limited to light source having a wavelength of 2940 nm. As stated previously, laser light of this wavelength can be provided by a Er:YAG light source, which is very expensive. Moreover, such a light source is relatively large, with the result that it would not be practical for use in a hand-held device.

It would be desirable to provide a method for providing an opening in the surface of the skin wherein an inexpensive light source is utilized, wherein the light source is of a size small enough to be portable and holdable in the hand of the user.

SUMMARY OF THE INVENTION

This invention provides an article capable of both collecting interstitial fluid and detecting an analyte in that fluid. Preferably, the article is also capable of measuring the amount of analyte in the interstitial fluid. The article can be used in conjunction with a meter that contains an appropriate detection element for determining the amount of analyte in the interstitial fluid. In one preferred embodiment, the article is a multiple-layer element comprising:

(1) a layer that is capable of being placed in contact with the skin of a patient;
(2) an overcoat layer that is coated over the skin-contacting layer;
(3) a layer, substantially coplanar with the overcoat layer, that is capable of transporting interstitial fluid by means of chemically aided wicking;
(4) a layer, overlying the interstitial fluid transporting layer, that is capable of being placed in contact with a meter, which layer has an opening therein through which light can be transmitted;
(5) a layer in communication with the interstitial fluid transporting layer, which layer is capable of detecting the presence of analyte or measuring the amount of analyte in the interstitial fluid.

In order to use the multiple-layer element, light from a source of light is transmitted through the opening in the multiple-layer material to be absorbed at a light-absorbing target on the skin-contacting layer. This light transfers energy to the target, and this transferred energy causes an opening to form in the skin-contacting layer and an opening to form in the stratum corneum. Interstitial fluid exudes from the opening in the stratum corneum and contacts the interstitial fluid transporting layer. The interstitial fluid then moves along or through the interstitial fluid transporting layer to the detecting layer. Preferably, the detecting layer comprises an electrochemical sensor or an optical sensor.

The multiple-layer element integrates the light-absorbing target, the skin-contacting layer, the overcoat layer, the fluid-transporting layer, the meter-contacting layer, and the detecting layer into one element. This integrated element can be made at a low enough cost to be disposable.

The collection of the interstitial fluid by this invention is less painful than is collection initiated by lancing with a conventional lancet. The patient is not required to handle the interstitial fluid. Consequently, sample placement errors are greatly reduced. Furthermore, a smaller sample of interstitial fluid is needed because no fluid is spilled during transfer of the fluid to a detector.

DETAILED DESCRIPTION

As used herein, the expression "interstitial fluid" is intended to include clear fluid that occupies the space between the cells in the body. The term "stratum corneum" means the outermost layer of the skin, consisting of from about 15 to about 20 layers of cells in various stages of drying out. The stratum corneum provides a barrier to the loss of water from inside the body to the external environment and from attack from the external environment to the interior of the body. The term "epidermis" means the metabolically active region of the skin. It is found just below the stratum corneum and is approximately 10 times as thick as the stratum corneum. The epidermis does not contain blood. The term "dermis" means the region of skin approximately 10 times as thick as the epidermis and found just below the epidermis. The dermis contains large amounts of collagen, which provides structural integrity to the skin. The dermis contains a layer of small blood capillaries that provide oxygen and nutrients to the rest of the layers of skin. The term "coplanar" means that at least one surface of each of two materials resides in the same plane.

In one preferred embodiment, the article of this invention comprises:

(1) a layer that is capable of being placed in contact with the skin of a patient;
(2) a layer that is coated over the skin-contacting layer;
(3) a layer, substantially coplanar with the overcoat layer, that is capable of transporting interstitial fluid by means of chemically aided wicking;
(4) a layer, overlying the interstitial fluid transporting layer, that is capable of being placed in contact with a meter, which layer has an opening therein through which light can be transmitted;
(5) a layer in communication with the interstitial fluid-transporting layer, which layer is capable of detecting the presence of analyte or measuring the amount of analyte in the fluid.

Figure 1:
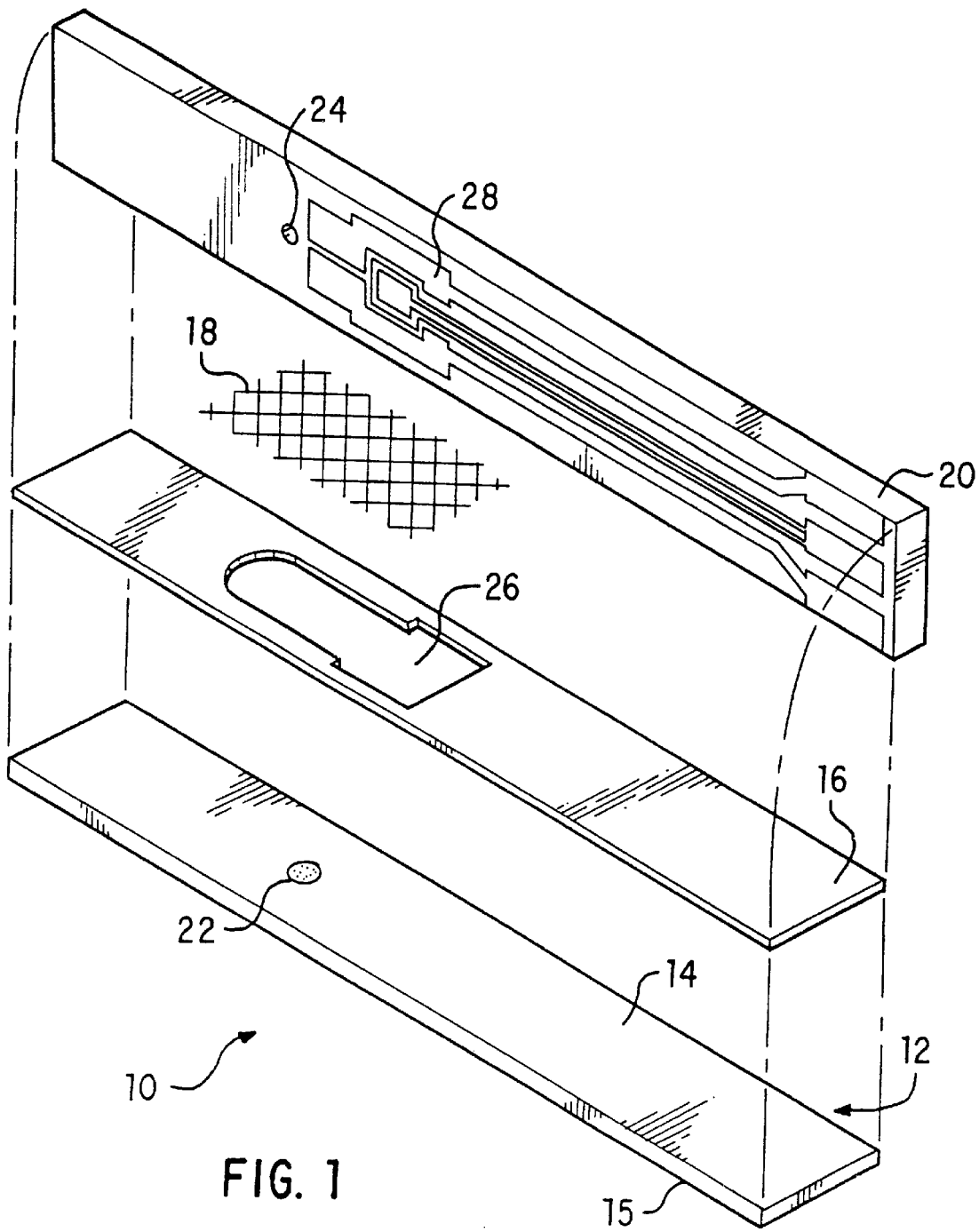
FIG. 1 depicts an exploded view of a multiple-layer element for collecting interstitial fluid and detecting an analyte. In this exploded view, the various layers are depicted in a peeled-apart orientation, whereby the interior major surfaces of the outermost layers face each other. In this view, the detecting layer employs a biosensor.
Figure 2:
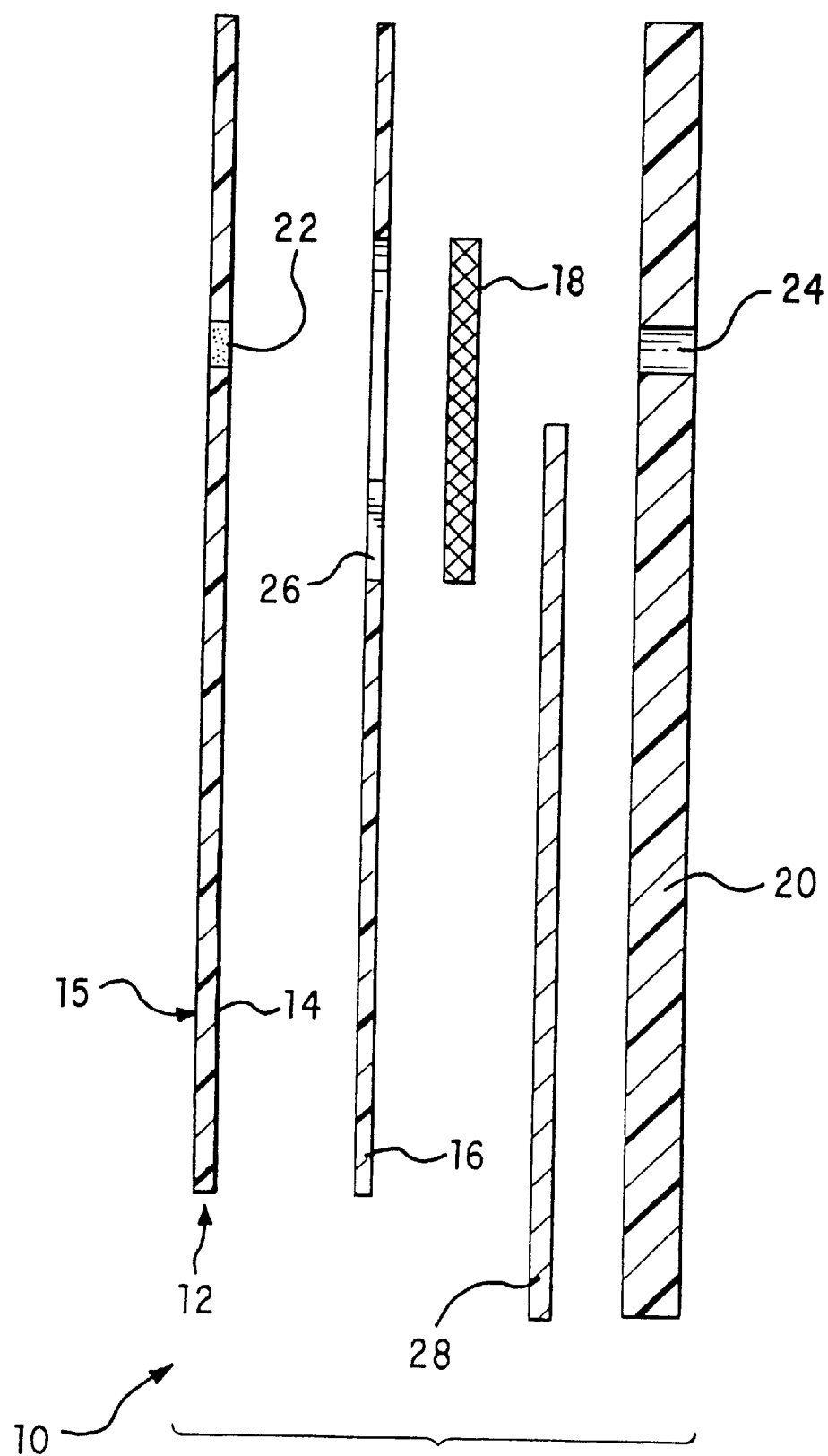
FIG. 2 depicts an exploded cross-sectional view a multiple-layer element for collecting interstitial fluid and detecting an analyte. In this view, the detecting layer employs a biosensor.

FIGS. 1 and 2 illustrate a preferred embodiment of the present invention. The article 10 comprises a skin-contacting layer 12. To one major surface 14 of skin-contacting layer 12 is adhered an overcoat layer 16. The other major surface 15 of the skin-contacting layer 12 is the surface that actually comes in face-to-face contact with the skin. Coplanar with the overcoat layer 16 is a layer 18 capable of transporting interstitial fluid by means of chemically aided wicking. Overlying layer 18 is a meter-contacting layer 20.

Figure 3:
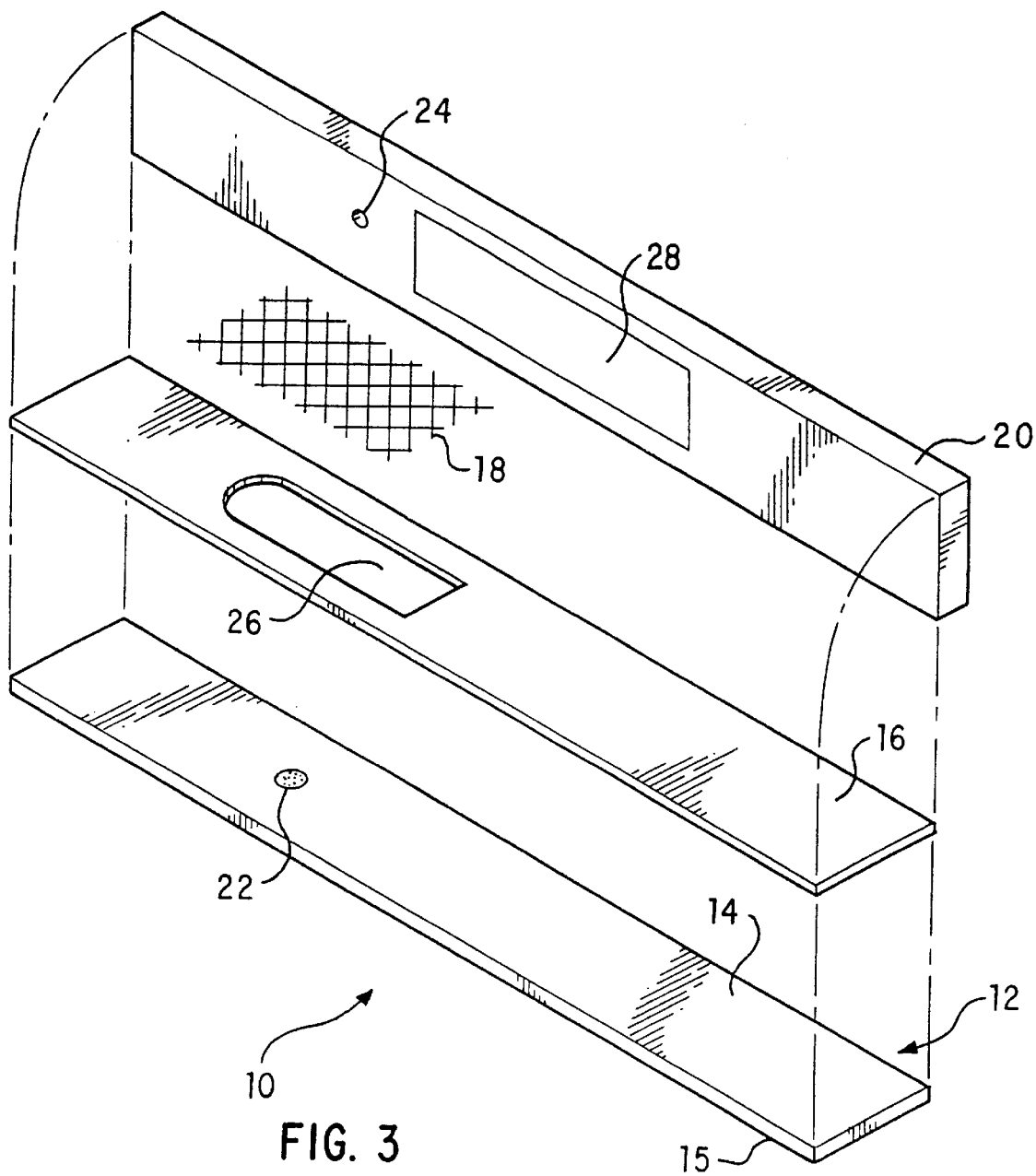
FIG. 3 depicts an exploded view of a multiple-layer element for collecting interstitial fluid and detecting an analyte. In this exploded view, the various layers are depicted in a peeled-apart orientation, whereby the interior major surfaces of the outermost layers face each other. In this view, the detecting layer employs a reflectance strip.
Figure 4:
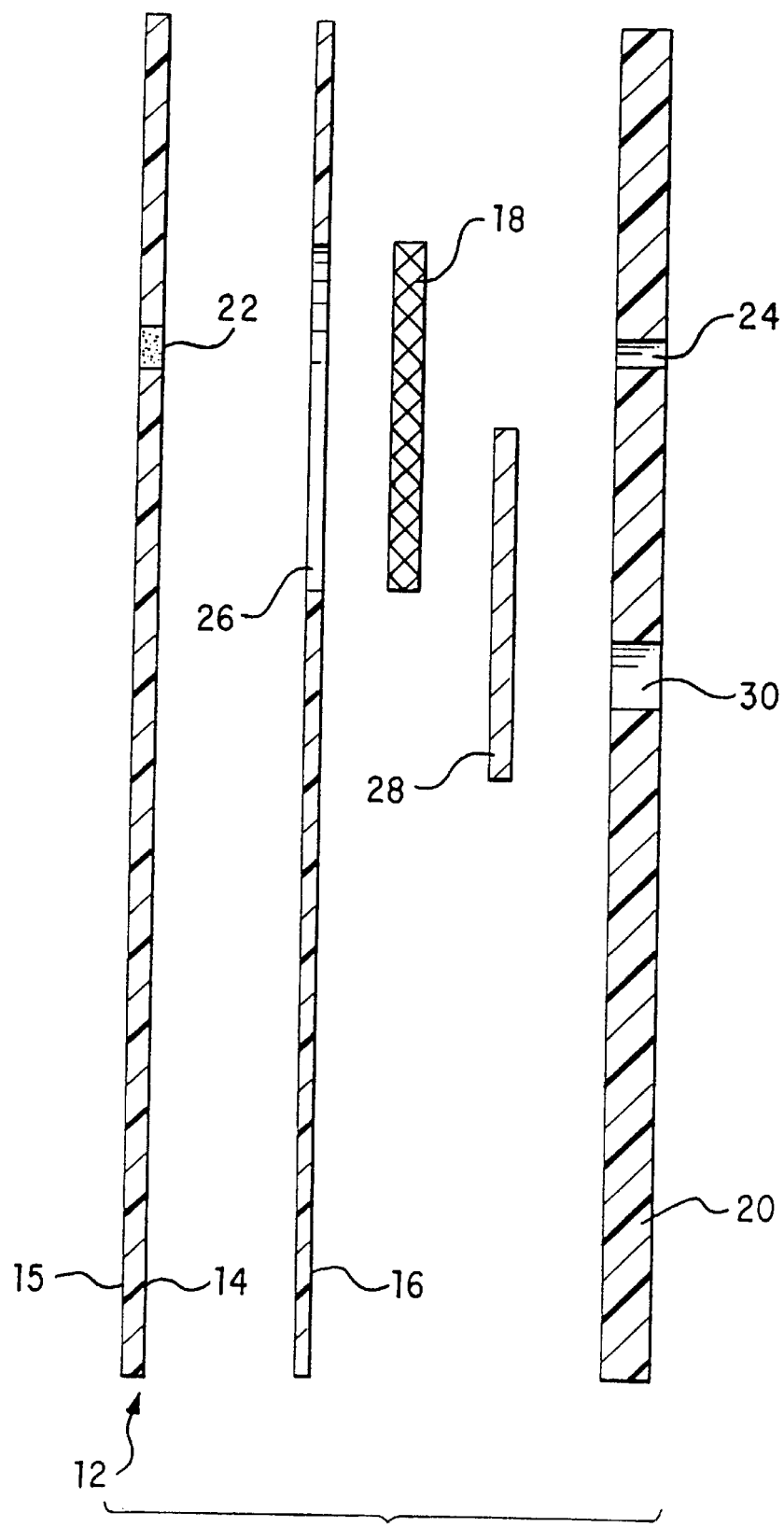
FIG. 4 depicts an exploded cross-sectional view a multiple-layer element for collecting interstitial fluid and detecting an analyte. In this view, the detecting layer employs a reflectance strip.

Skin-contacting layer 12 has a laser target 22 indicated thereon. While FIGS. 1, 2, 3, and 4 refer to a laser target, it should be noted that the source of light need not be a laser. However, for the sake of simplification, the source of light will be referred to as a laser. Other sources of light, such as, for example, flash lamps, i.e., pulsed high intensity white light, may also be used. The meter-contacting layer 20 has an opening 24 formed therethrough. The laser target 22 and the opening 24 are aligned so that a laser beam can pass through the opening 24 and strike target 22. The interstitial fluid-transporting layer 18 can be designed to allow the laser beam to pass through it. The overcoat layer 16 has an opening 26 formed therein so that interstitial fluid can be transported from an opening in the stratum corneum, through the opening formed by destruction of the target 22 by laser, to the interstitial fluid transporting layer 18, and then along the interstitial fluid transporting layer 18 to a detecting layer 28. Disposed on the meter-contacting layer 20 is a detecting layer 28, which comprises a layer or layers of chemicals capable of reacting with an analyte in a biological fluid to produce either a measurable electrical response or a measurable optical response. U.S. Pat. Nos. 4,545,382 and 4,711,245 describe detecting layers capable of generating a measurable electrical signal in response to glucose in blood. See FIGS. 1 and 2. U.S. Pat. Nos. 4,935,346 and 4,929,545 describe detecting layers capable of producing a measurable change in reflectance in response to glucose in biological fluid. See FIGS. 3 and 4. In FIGS. 3 and 4, an opening 30 is provided in the meter-contacting layer 20 so that the change in reflectance in response to glucose in biological fluid can be measured. Alternatively, the detecting layer 28 can be disposed on the surface 14 of the skin-contacting layer 12.

The target 22 is preferably formed of a photosensitizing material adhered to or combined with a carrier material. Photosensitizing materials suitable for use in this invention are capable of absorbing electromagnetic radiation at one or more wavelengths. Electromagnetic radiation considered to be suitable for this invention include radiation from the ultraviolet, visible and infrared regions of the electromagnetic spectrum. It is preferred, however, that visible radiation and infrared radiation be employed. Ultraviolet radiation has a wavelength ranging from about 10 nm to about 380 nm. Visible radiation has a wavelength ranging from about 380 nm to about 780 nm. Infrared radiation has a wavelength ranging from about 780 nm to about 300,000 nm. Photosensitizing materials suitable for use in this invention include, but are not limited to, dyes and pigments. The term "pigment" is used to describe the class of colorants that are practically insoluble in the media in which they are applied. Pigments retain a particulate form, suspended in the media. The term "dye" is used to describe colorants that are soluble, or at least partially soluble, in the media in which they are applied. Dyes exhibit an affinity to the substrate to which they are applied. Classes of dyes that are suitable for use in this invention include, but are not limited to, diphenylmethane dyes, methine-polymethine dyes, porphine dyes, indathrene dyes, quinones, dithiol metal complexes, dioxazines, dithiazines, polymeric chromophores. Classes of pigments that are suitable for use in this invention include, but are not limited to, carbon black, carbon based pigments, metals, metal sols, dyed latexes, inorganic pigments. Colorants that are preferred for this invention include, but are not limited to, copper phthalocyanine, indocyanine green, nigrosin, prussian blue, colloidal silver (20 to 100 nm diameter), carbon black, IR-780, IR-140, irgalan black, naphthol green B, tellurapyryllium, and vanadyl tetra-t-butyl-naphthalocyanine. In either case, particles of the dyes or pigments must be of a size that they can readily be blended with carrier materials. Carrier materials suitable for use with dyes and pigments include, but are not limited to, solid polymers, adhesives, gels, inks. These materials comprise polymeric materials such as acrylics, silicones, polyesters, polycarbonates, polyimides, cellulose, derivatives of cellulose, polyvinyl derivatives, polyethylenes, polypropylenes, and the like. It is preferred that the particles of pigments have a major dimension, e.g., length, diameter, no greater than about 50 $\mu$m.

The photosensitizing material should not adversely affect the patient. The photosensitizing material should be able to withstand elevated temperatures. The photosensitizing material preferably does not melt or decompose at temperatures below about 120° C. The photosensitizing material should be capable of absorbing a sufficient amount of light to convert it to an amount of thermal energy sufficient to cause permeation of the tissue.

In one embodiment of this invention, the photosensitizing material can be applied to the skin-contacting layer by means of a carrier. The carrier is a material in which the photosensitizing material can be uniformly dissolved, if a dye, or uniformly suspended, if a pigment. Carriers that are suitable for uniformly dissolving dyes include, but are not limited to, solid polymers, adhesives, gels, inks. Carriers that are suitable for uniformly suspending pigments include, but are not limited to, solid polymers, adhesives, gels, inks. The concentration of photosensitizing material in the carrier can vary. However, that concentration must be sufficient to provide the level of energy required for the desired function within the desired period of time. For example, if the desired function is to permeate the stratum corneum, and the selected photosensitizing material is carbon black, and the selected carrier is acrylic adhesive, and the selected source of energy is a laser diode (e.g., 810 nm), then the concentration of photo-sensitizing material in the carrier should be sufficient to absorb at least 10% of the input energy, preferably 50% of the input energy, more preferably 90% of the input energy. This parameter can also be expressed in terms of the amount of thermal energy generated per volume of photosensitizing assembly in joules per cubic centimeter. A sufficient concentration of dye is typically that required to obtain an optical density greater than 1.0 at the wavelength of the laser. Determination of the appropriate concentration can readily be determined by trial-and-error by one of ordinary skill in the art.

In addition to the photosensitizing material, other ingredients that can be added to the carrier include, but are not limited to, plasticizers, surfactants, binders, crosslinking agents. These materials are commercially available.

Substrates, i.e., skin-contacting layers, to which the carrier containing the photosensitizing material can be applied include, but are not limited to, polymeric materials, cloth, non-woven materials, microporous membranes, glass, metal foils. The substrate is preferably sufficiently flexible to allow close contact with the tissue. The substrate should adhere sufficiently to the carrier so that the carrier does not become detached from the substrate before or during use. Both the substrate and the carrier should be biocompatible so that neither of them adversely affect the patient. Representative examples of materials that are suitable for preparing the substrate include, but are not limited to, polyesters, polyimides, polyethylenes, polypropylenes, polycarbonates, polyacrylics, and combinations thereof.

In another embodiment wherein the photosensitizing material is blended with a film-forming material to form the skin-contacting layer, the film-forming material is preferably capable of being formed into a film that will allow uniform suspension of the photosensitizing material and will allow sufficient flexibility to conform to the tissue of the patient. Film-forming materials suitable for use in this embodiment include, but are not limited to, polyesters, polyimides, polyethylenes, polypropylenes, polycarbonates, polyacrylics, and combinations thereof.

The thickness of the skin-contacting layer is not critical, but preferably ranges from about 0.005 mm to about 2.0 mm. The surface dimensions of this layer are not critical, but the major dimension preferably ranges from about 5 mm to about 60 mm and the minor dimension preferably ranges from about 2 mm to about 30 mm in width. The layer is shown as being rectangular, but other shapes are also suitable, e.g., circular, elliptical, triangular, square, and other shapes. The skin-contacting layer 12 can be adhered to the skin of the patient by means of adhesive, electrostatic force, or pressure applied by the patient. The seal between the skin and the skin-contacting layer 12 should be sufficiently tight so that interstitial fluid does not leak through it.

The target 22 of the skin-contacting layer 12 is capable of absorbing light. The target 22 of the skin-contacting layer 12 must absorb a sufficient amount of light energy, which is transformed to thermal energy, to result in formation of an opening in the stratum corneum. During the formation of the opening in the stratum corneum, the target is ablated. The laser is ineffective after the target is ablated. The size of the target 22 can vary. The size of the target can be larger than the light beam or smaller than the light beam. If the light beam is used to define the size of the opening to be formed in the stratum corneum, it is preferred that the target be relatively large so that the light can easily strike the target. If the target size is used to define the size of the opening in the stratum corneum, it is preferred that the size of the target be smaller than the size of the light beam. The material of which the target 22 is formed must be capable of being removed by exposure to light energy to form the opening in the stratum corneum so that interstitial fluid can reach the interstitial fluid-transporting layer 18.

There are several ways to prepare the skin-contacting layer and the light target coated thereon. According to one method, a pigment, e.g., carbon black, can be suspended uniformly into a pressure-sensitive adhesive composition. The adhesive composition can then be cast, or printed, onto a polymeric substrate. The adhesive composition can then be cured. According to another method, a dye, e.g., copper phthalocyanine, can be suspended in an organic solvent, e.g., ethanol. The suspension can be applied to one side of a polymeric membrane by means of an air-brush. The film can then be allowed to dry. According to a third method, a pigment, e.g., carbon black, can be suspended in a polymer based ink, such as clear nail polish. The ink can then be cast, or printed, onto a polymeric substrate. The film can then be cured. According to still another method, a pigment, e.g., carbon black, can be blended into a polymeric material, e.g., linear low density polyethylene. The blend can then be melted and extruded into a film. The film can then be cured to form the skin-contacting layer. Regardless of how the skin-contacting layer is prepared, the major surface 15 is the major surface that is intended to come into contact with the skin.

The overcoat layer 16 is preferably formed from a polymeric material. Representative examples of polymeric materials suitable for preparing the overcoat layer include, but are not limited to, polymers formed from acrylic monomers, methacrylic monomers, acrylate monomers, methacrylate monomers, and combinations thereof. The overcoat layer is adhered to the skin-contacting layer preferably by means of lamination or screen printing.

The interstitial fluid transporting layer 18 transports interstitial fluid by means of a chemically aided wicking action. As used herein, the expression "chemically aided wicking action" means the flow of fluid along a material while being aided by at least one chemical substance that is present on the surface of that material. As used herein, the expression "chemically aided wicking action" refers to either:

(a) the flow of fluid along a material wherein the nature of the material itself is hydrophilic, such as, for example, cellulose;

(b) the flow of fluid along a material wherein at least one chemical substance is applied to the surface of the material, such as, for example, nylon coated with surfactant;

(c) the flow of fluid along a material that has been rendered hydrophilic by means of a chemical or physical process, such as, for example, treatment of polyester by means of corona discharge treatment, plasma treatment, flame treatment, or the like.

The purpose of the at least one chemical substance is to promote the flow of fluid along the surface of the material. Chemical substances suitable for the surface of the interstitial fluid transporting layer belong to the class of compounds commonly referred to as surfactants. A surfactant reduces the surface tension of a liquid that contacts a surface upon which the surfactant is coated and allows the coated surface to attract rather than repel fluids. A commercially available surfactant suitable for use in this invention is a fluorochemical surfactant having the trade designation "FC 170C FLUORAD", available from Minnesota Mining and Manufacturing Company, St. Paul, Minn. This surfactant is a solution of a fluoroaliphatic oxyethylene adduct, lower polyethylene glycols, 1,4-dioxane, and water. The interstitial fluid transporting layer can be made from polymeric material. Representative examples of polymeric material suitable for this invention include, but are not limited to, polymers formed from amide monomers, e.g., nylon, ester monomers, alkylene monomers, e.g., polypropylene, polyethylene, cellulosic monomers, and combinations thereof. The amount of surfactant is not critical but it is preferred that the amount of surfactant range from 1 to 10 $\mu$g surfactant per mg of material of the interstitial fluid transporting layer. The preferred surfactant loading may vary depending upon the nature of the material of the interstitial fluid-transporting layer and the surfactant used. The preferred amount can be determined empirically by observing flow of sample along the interstitial fluid-transporting layer with different levels of surfactant loading. The surfactant may not be necessary if the mesh is made of hydrophilic material.

The interstitial fluid transporting layer must be capable of allowing light from the light source to pass through it. The interstitial fluid transporting layer can be transparent to light, whereby light travels through the interstitial fluid transporting layer. The interstitial fluid transporting layer can be a mesh, whereby the light travels between the strands of the mesh. The interstitial fluid transporting layer can have a small hole in it, whereby the light passes through that hole. The interstitial fluid transporting layer must be capable of allowing a sufficient amount of interstitial fluid to uniformly flow through it at a rate sufficiently great that a sufficient amount of fluid reaches the detecting layer before evaporation causes the size of the sample to be inadequate to provide a reading of glucose level within a reasonable time.

The interstitial fluid transporting layer is preferably made from polymeric material, cellulosic material, natural fibrous material, or an equivalent material. Representative examples of polymeric materials suitable for the interstitial fluid transporting layer of this invention include, but are not limited to, polymers comprising amide monomeric units, e.g., nylon, ester monomeric units, alkylene monomeric units, e.g., polypropylene, polyethylene, cellulosic monomeric units, and combinations thereof. The interstitial fluid transporting layer can be a mesh. The mesh is preferably constructed of finely woven strands of polymeric material; however, any woven or non-woven material may be used, provided that the interstitial fluid-transporting layer transports the interstitial fluid to the detecting layer before the interstitial fluid evaporates or clots. A fine mesh that is suitable for the multiple-layer element of this invention has a percent open area of from about 40 to about 45%, a mesh count of from about 95 to about 115 fibers per cm, a fiber diameter of from about 20 to about 40 $\mu$m, and a thickness of from about 40 to about 60 $\mu$m. A particularly preferred mesh is NY64 HC mesh, available from Sefar (formerly ZBF), CH-8803, Ruschlikon, Switzerland. A coarse mesh that is suitable for the multiple-layer element of this invention has a percent open area of from about 50 to about 55%, a mesh count of from about 45 to about 55 fibers per cm, a fiber diameter of from about 55 to about 65 $\mu$m, and a thickness of from about 100 to about 1000 $\mu$m. A preferred mesh is NY151 HC mesh, available from Sefar (formerly ZBF), CH-8803, Ruschlikon, Switzerland. Mesh characteristics are further described in U.S. Pat. No. 5,628,890, incorporated herein by reference.

The interstitial fluid transporting layer is capable of allowing a sufficient amount of interstitial fluid to uniformly flow through it at a rate sufficiently great that a sufficient amount of interstitial fluid, e.g., 0.1 to 10 $\mu$l, preferably up to 2 $\mu$l, more preferably up to 1 $\mu$l, reaches the detecting layer before evaporation causes the size of the sample to be inadequate to provide a reading of analyte level within a reasonable time, e.g., up to five minutes. The interstitial fluid transporting layer can be adhered to the covering layer by means of hot melt adhesive on the major surface of the covering layer that faces the meter-contacting layer.

Figure 6:
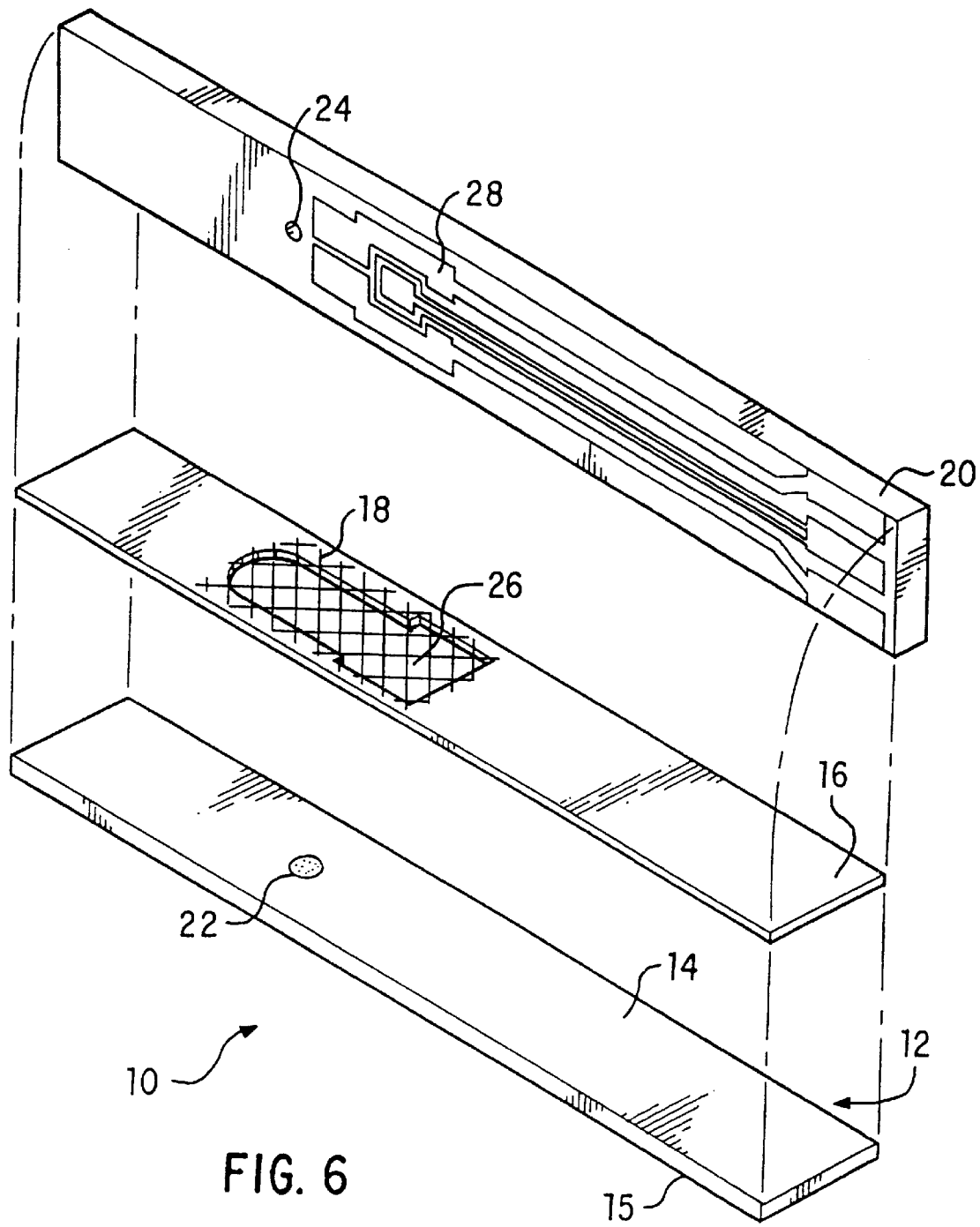
FIG. 6 depicts an exploded view of a multiple-layer element for collecting interstitial fluid and detecting an analyte. In this exploded view, the various layers are depicted in a peeled-apart orientation, whereby the interior major surfaces of the outermost layers face each other. In this view, the detecting layer employs a biosensor.
Figure 7:
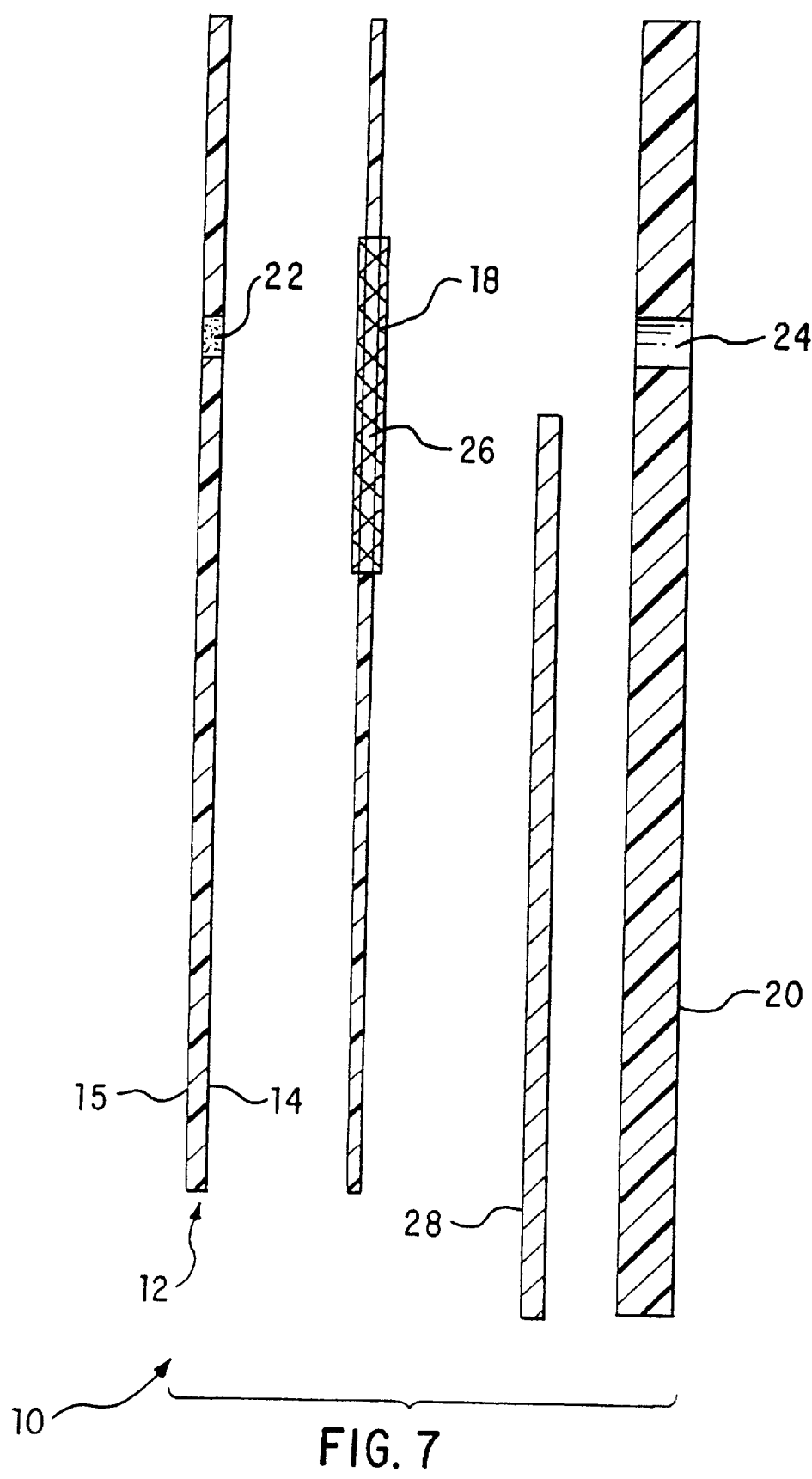
FIG. 7 depicts an exploded cross-sectional view a multiple-layer element for collecting interstitial fluid and detecting an analyte. In this view, the detecting layer employs a biosensor.

The overcoat layer 16 and the interstitial fluid transporting layer 18 are substantially coplanar. Substantial coplanar positioning of these layers is preferred because the interstitial fluid transporting layer 18 spreads fluids in all directions. In order to limit the spread of fluid in undesired areas of the multiple-layer element, the overcoat layer acts as a barrier to flowing fluid. The edges of the interstitial fluid transporting layer 18 are embedded in the overcoat layer 16, thereby preventing the flow of fluid when the fluid reaches the overcoat layer. The interstitial fluid transporting layer 18 is adhered to the skin-contacting layer 12 by means of embedding the edges of the interstitial fluid transporting layer 18 with the overcoat layer 16. FIGS. 6 and 7 illustrate the relationship between the planes of the overcoat layer 16 and the interstitial fluid transporting layer 18. As used herein, the expression "substantially coplanar" includes both the situation wherein at least one major surface of the overcoat layer 16 and at least one major surface of the interstitial fluid transporting layer 18 are in the same plane and the situation wherein at least one major surfaces of the overcoat layer 16 extends slightly beyond at least one major surface of the interstitial fluid transporting layer 18. See FIG. 7. True coplanarity, i.e., the former situation, is difficult to achieve primarily because of manufacturing conditions. Substantial coplanarity, i.e., the latter situation, is more likely to be achieved under actual manufacturing conditions. FIGS. 6 and 7 illustrate the more likely manufacturing result. However, it is preferred that the overcoat layer 16 and the interstitial fluid transporting layer 18 approach true coplanarity as much as possible so that the volume of interstitial fluid needed to be extracted is as small as possible.

The detecting layer 28 preferably comprises an electrochemical detector, e.g., a biosensor, or an optical detector, e.g., a reflectance detector. The detecting layer is supported on either the skin-contacting layer or on the meter-contacting layer. The detecting layer comprises a layer or layers of chemicals, e.g., an enzyme, capable of reacting with an analyte in a biological fluid to produce either a measurable electrical response or a measurable optical response. An example of a detecting layer is described in U.S. Pat. No. 5,682,884. The detecting layer described in U.S. Pat. No. 5,682,884 comprises a first conductor and a second conductor extending along a support and further comprises a means for connection to readout circuitry. An active electrode, positioned to contact the liquid interstitial fluid sample and the first conductor, comprises a deposit of an enzyme capable of catalyzing a reaction involving the analyte compound, e.g., glucose, in the liquid interstitial fluid sample. Electrons are transferred between the enzyme-catalyzed reaction and the first conductor to create the current. A reference electrode is positioned to contact the liquid interstitial fluid sample and the second conductor.

Detecting layers of the electrochemical type should be non-porous. Detecting layers of the optical type are preferably porous. It is also preferred that the detecting layer be flexible, so that it will conform to whichever layer to which it is applied, the skin-contacting layer or the meter-contacting layer. Detecting layers of the electrochemical type can be transparent or non-transparent. Detecting layers of the optical type are preferably reflective. The detecting layer must also contain the reagents required for the chemical reaction required to provide an indication of the concentration or presence of analyte. In the case of glucose monitoring, these reagents include, but are not limited to, ferrocene, ferricyanide, glucose oxidase, glucose dehydrogenase, and peroxidases. Detecting layers of the electrochemical type can preferably comprises a member selected from the group consisting of carbon, platinum, gold, palladium, silver chloride, and silver. Detecting layers of the reflectance type can comprise at least one dye and at least one enzyme.

As stated previously, a typical detecting layer comprises a first conductor and a second conductor extending along a support and further comprises a means for connection to readout circuitry. An active electrode, positioned to contact the liquid interstitial fluid sample and the first conductor, comprises a deposit of an enzyme capable of catalyzing a reaction involving the analyte compound, e.g., glucose, in the liquid interstitial fluid sample. Electrons are transferred between the enzyme-catalyzed reaction and the first conductor to create the current. A reference electrode is positioned to contact the liquid interstitial fluid sample and the second conductor.

In a preferred embodiment of a detecting layer for the multiple-layer element of this invention, an electron mediator, e.g., a ferrocene, is included in the active electrode deposit to effect the electron transfer. The compound being detected is glucose and the enzyme is glucose oxidase or glucose dehydrogenase. The active electrode and the reference electrode are coatings applied to the skin-contacting layer or to the meter-contacting layer. For example, the active electrode is formed by printing (e.g., screen printing) an ink comprising a conductive compound, the enzyme, and the mediator, and the reference electrode is also formed by printing (e.g., screen printing). The means for connecting to the readout circuit are positioned toward one end of the skin-contacting layer or the meter-contacting layer, and the electrodes are positioned remote from that end.

The meter-contacting layer 20 is preferably made from a polymeric material. Representative examples of polymeric material suitable for preparing the meter-contacting layer include, but are not limited to, polymers formed from acrylic monomers, methacrylic monomers, acrylate monomers, methacrylate monomers, vinyl chloride monomers, and combinations of the foregoing. Other polymers suitable for preparing the meter-contacting layer include polyesters. The overcoat layer is adhered to the meter-contacting layer preferably by means of lamination or screen printing. The functions of the meter-contacting layer are to (1) provide a surface on which to print the detecting layer, (2) provide alignment of the laser target on the multiple-layer article with the laser light source, (3) provide contact of the multiple-layer article with the meter for the purpose of reading the signal from the detecting portion of the multiple-layer article, (4) provide a rigid layer so that the multiple-layer article can be easily picked up and placed in contact with the meter. If the detecting layer is disposed on the surface 14 of the skin-contacting layer 12, the meter-contacting layer 20 would not perform the first and third listed functions, but would continue to perform the second and fourth listed functions.

The following table lists suitable ranges for the dimensions of the layers of the multiple-layer article of this invention. It is not intended that the dimensions of the layers of the multiple-layer article of this invention be limited to the ranges listed in the following table.

TABLE I

| Layer | Major surface dimension (mm) | Minor surface dimension (mm) | Thickness (mm) |
| --- | --- | --- | --- |
| Skin-contacting | 60 to 5 | 2 to 30 | 0.005 to 2.0 |
| Overcoat | 60 to 5 | 2 to 30 | 0.05 to 0.5 |
| Fluid transporting | 60 to 5 | 2 to 30 | 0.005 to 0.5 |
| Detecting | 60 to 5 | 2 to 30 | 0.001 to 0.5 |
| Meter-contacting | 60 to 5 | 2 to 30 | 0.05 to 2.0 |

The multiple-layer article must be sufficiently flexible so that it can conform to the shape of a body part. The multiple-layer article must be sufficiently rigid so that it can be easily handled by the user. In the preferred embodiments, at least one of the skin-contacting layer 12 and the meter-contacting layer 20 should be made of a material that is sufficiently flexible to conform to the shape of a body part, but is still sufficiently rigid to support the overcoat layer, the interstitial fluid transporting layer, and the detecting layer. The last three mentioned layers can be extremely flexible and of minimal rigidity.

The porosity of the layers of the multiple-layer article is dependent upon the positioning and functionality of the layer. The skin-contacting layer, the overcoat layer, the meter-contacting layer should be sufficiently non-porous to form a well or chamber for the interstitial fluid. The interstitial fluid transporting layer should be sufficiently porous to allow interstitial fluid to flow uniformly and rapidly therethrough to the detecting layer. The porosity of the detecting layer is not critical; it can be porous or non-porous depending upon the design selected by the manufacturer.

The opacity of the skin-contacting layer is not critical unless the target is on the surface of the skin-contacting layer that contacts the skin, in which case the skin-contacting layer must be transparent to the electromagnetic radiation of the laser.

The surface dimensions of the overcoat layer are preferably identical to that of the skin-contacting layer. The opacity of the overcoat layer is not critical.

The surface dimensions of the fluid transporting layer are preferably less than those of the meter-contacting layer so that the electrical contacts are exposed to facilitate insertion into the meter. The opacity of the fluid transporting layer is not critical unless the electromagnetic radiation from the laser is transmitted through it, in which case, the fluid transporting layer must be transparent to the electromagnetic radiation of the laser.

The surface dimensions of the meter-contacting layer are preferably larger than those of the skin-contacting layer so that electrical contacts, in the case of electrochemical sensors, are exposed for insertion into the meter. The opacity of the meter-contacting layer is not critical unless photometric detection is used.

Method for Preparing the Multiple-Layer Article

The multiple-layer article is preferably mass-produced. However, the following method can be used for the manufacture of a single multiple-layer article.

The meter-contacting layer 20 is provided in the form of a sheet. In a typical construction, the meter-contacting layer 20 is a sheet of polyvinyl chloride. The opening 24 is formed in the meter-contacting layer 20, preferably by means of die cutting, laser cutting, punching, drilling, or the like. The detecting layer 28 is screen printed onto the meter-contacting layer 20. The detecting layer 28 is a biosensor of a type described in U.S. Pat. No. 4,545,382, incorporated herein by reference. The electrodes of the detecting layer 28 contain a biologically active substance that reacts with glucose, preferably glucose oxidase or glucose dehydrogenase, at an electrically conductive material, preferably carbon, which caries the electrical signal produced by the reaction of glucose with the biologically active substance. The generation of the electrical signal may be aided by compounds known as mediators, which increase the electrical signal. See Ferrocene-Mediated Enzyme Electrode for Amperometric Determination of Glucose, Anal. Chem. 1984, 56, 667–671. The electrical circuit is completed with at least one other electrically conductive material, preferably carbon. The interstitial fluid-transporting layer 18 is then placed in a position such that it will be in fluid communication with the detecting layer 28. The overcoat layer 16 is then screen printed onto the meter-contacting layer 20 and cured in a curing oven. A template or the like can be used so that the cured overcoat layer does not block the interstitial fluid from reaching the interstitial fluid-transporting layer 18. Finally, the skin-contacting layer 10 is applied over the overcoat layer 16 and bonded to the overcoat layer 16, preferably by a thermally curable adhesive or a thermally setting adhesive.

Operation

Figure 5A:
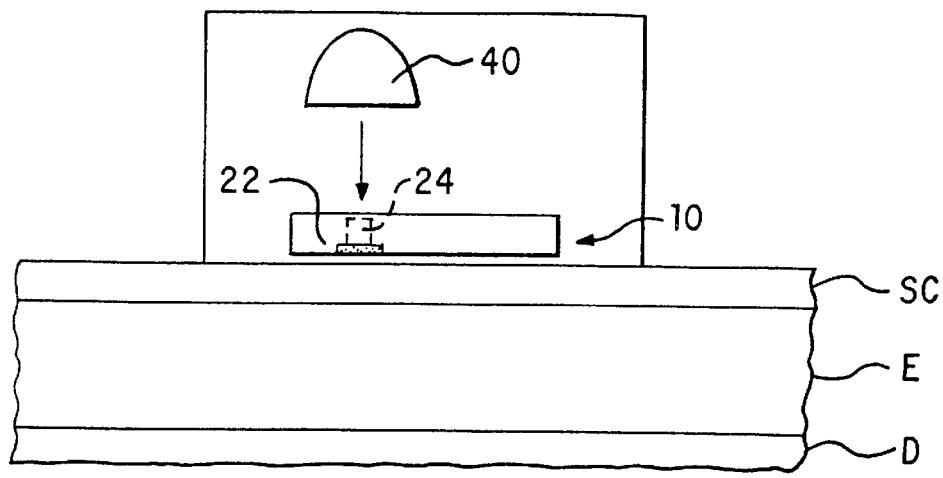
FIGS. 5A, 5B, and 5C schematically illustrate a procedure by which the method of this invention is carried out.
Figure 5B:
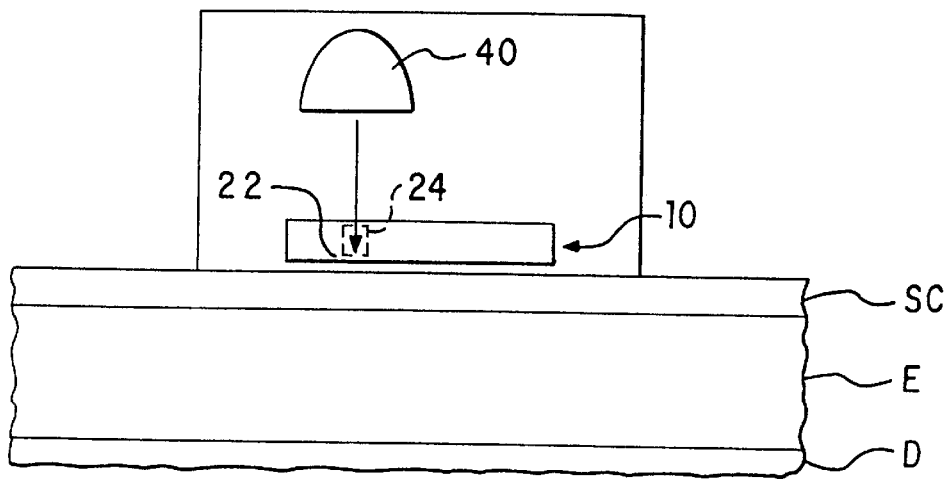
Figure 5C:
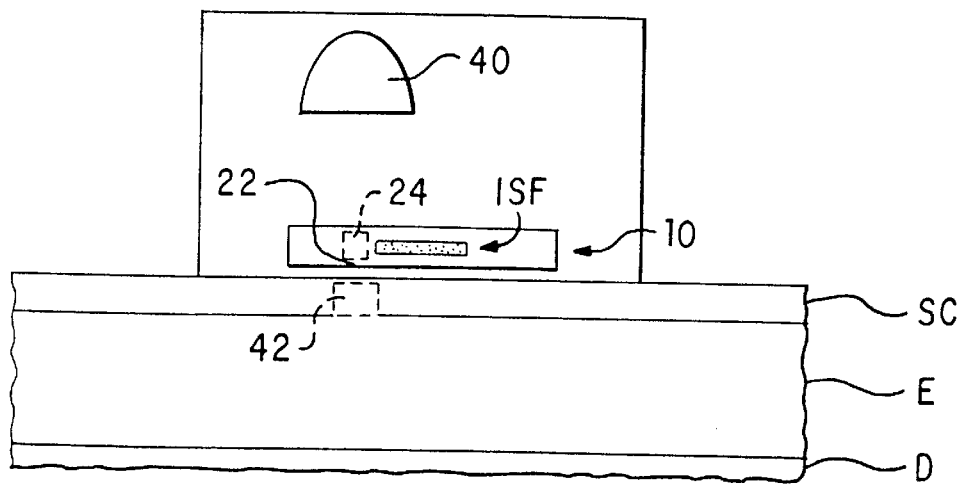

FIGS. 5A, 5B, and 5C illustrate the operation of the present invention. In order to use the article of this invention for detecting the presence or amount of analyte in a sample of interstitial fluid, the major surface of the skin-contacting layer of the multiple-layer article 10 that actually comes in face-to-face contact with the skin is placed against a surface of the skin of a patient. In FIGS. 5A, 5B, and 5C, the stratum corneum is represented by the letters "SC", the epidermis is represented by the letter "E", and the dermis is represented by the letter "D." Then, the source of light 40, typically a pulsed laser, is activated. The light from the source of light 40 is transmitted through the opening 24 in the multiple-layer article 10 and then it strikes the target 22 of the multiple-layer article 10. After an appropriate period of time, e.g., from about 10 ms to about 1 second, the energy generated by the source of light heats the target, and the thermal energy transferred forms an opening 42 in the skin. The opening 42 should extend all the way through the stratum corneum but should terminate before reaching the dermis. If the opening 42 extends through the dermis, it is likely that blood will be collected along with the interstitial fluid. Interstitial fluid, represented in FIG. 5C by the letters "ISF", then traverses the stratum corneum through the opening 42 and is taken up by the interstitial fluid transporting layer. See details of the multiple-layer article 10 in FIGS. 1, 2, 3, 4, 6, and 7. The interstitial fluid flows through the interstitial fluid transporting layer, whereupon it reaches the detecting layer. A chemical reaction occurs at the detecting layer. The output of the chemical reaction can be read at a meter (not shown). In the case of an electrochemical sensor, the meter-contacting layer must physically contact the meter in order to have the sensor make electrical contact with the meter, such as by insertion into an electrical contact. The meter-contacting layer can also serve the purpose of physically aligning the multiple-layer article with the meter in order that the laser is properly aligned with the laser target. In the case of the reflectance strip, the meter-contacting layer must attach itself to the meter to allow alignment of the light source and the detector of the meter with the reflectance strip, as well as allowing physical alignment of the multiple-layer article with the meter so that the laser is aligned with the laser target.

Sources of light that are suitable for use with the article of this invention include, but are not limited to, lasers. Lasers suitable for forming an opening in the skin to draw biological fluid are well-known in the art. See for example, U.S. Pat. Nos. 4,775,361, 5,165,418, 5,374,556, International Publication Number WO 94/09713, Lane et al. (1984) IBM Research Report—"Ultraviolet-Laser Ablation of Skin", and WO 97/07734, all of which are incorporated herein by reference. Lasers that are suitable for forming an opening in the skin the skin include, but are not limited to, Er:YAG, Nd:YAG, HeNe, and semiconductor lasers. Flash lamps, e.g., sources of pulsed high intensity white light, are also suitable for use with the article of this invention.

By combining the skin-contacting layer, which contains the laser target, and the detecting layer by means of a interstitial fluid-transporting layer, the collection of interstitial fluid can be carried out in a highly efficient manner. Improving the efficiency of collection will reduce the period of time required to obtain interstitial fluid for analytical purposes.

The use of the interstitial fluid-transporting layer provides several advantages when compared with a capillary flow channel for transporting interstitial fluid. An example of such a capillary flow channel can be seen in the Bayer Glucometer Elite® test strip and in the device shown in U.S. Pat. No. 5,141,868. The interstitial fluid-transporting layer used in the present invention allows interstitial fluid obtained from a patient to contact the detecting layer of a multiple-layer element more quickly than would a capillary flow channel. In the case of a multiple-layer element utilizing an interstitial fluid-transporting layer, the interstitial fluid emerging from the opening in the skin directly contacts one major surface of the interstitial fluid-transporting layer and is rapidly transported to the detecting layer. In the case of a multiple-layer element utilizing a capillary flow channel, the interstitial fluid emerging from the opening in the skin must contact both of two opposing surfaces of the capillary flow channel. The latter type of contact not only requires a greater volume of sample, it also requires a greater duration of time.

In addition, the use of the interstitial fluid-transporting layer also makes it possible to utilize an opening in the meter-contacting layer. In the case of a multiple-layer element utilizing a capillary flow channel, an opening in the meter-contacting layer, which would form one surface of the capillary flow channel, would prevent the capillary flow channel from efficiently transporting interstitial fluid to the detecting layer. There are several advantages to using an opening in the meter-contacting layer. First, the source of light used to provide the energy to form the opening in the skin can be aimed so that the light can pass through the opening in the meter-contacting layer, thereby minimizing optical interference with the light from the meter-contacting layer. Second, the meter-contacting layer can be made from a material that is not transparent to the light from the source of light. Third, the opening in the meter-contacting layer allows a vacuum to be coupled to the multiple-layer element, thereby allowing suction to aid in extracting interstitial fluid from the opening in the skin. Fourth, the opening in the meter-contacting layer allows debris produced during the skin opening step of the method to be removed. This debris, if not removed, may deflect second and subsequent pulses of light from the source of light, with the result that insufficient energy will be available to form the opening in the skin.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. Method for collecting interstitial fluid and analyzing said fluid for an analyte, said method comprising the steps of:
    (a) providing a multiple-layer element comprising:
        (1) a layer that is capable of being placed in contact with the skin of a patient;
        (2) an overcoat layer that is coated over the skin-contacting layer;
        (3) a layer, substantially coplanar with the overcoat layer, that is capable of transporting interstitial fluid by means of chemically aided wicking;
        (4) a layer, overlying the interstitial fluid transporting layer, that is capable of being placed in contact with a meter, said layer having an opening therein through which light can be transmitted;
        (5) a layer in communication with the interstitial fluid transporting layer, which layer is capable of detecting the presence of analyte or measuring the amount of analyte in the fluid;
    (b) placing said element in contact with the skin;
    (c) providing a source of light;
    (d) transmitting light through said multiple-layer element such that said light causes an opening to be formed in the skin;

(e) collecting interstitial fluid in said fluid transporting layer;

(f) transporting interstitial fluid to said analyte detecting layer;

(g) detecting the presence of an analyte or measuring the amount of analyte in the fluid.

2. The method of claim 1, wherein said skin-contacting layer has a target for said light.

3. The method of claim 2, wherein said target comprises a dye or a pigment.

4. The method of claim 1, wherein said skin-contacting layer bears an adhesive on one major surface thereof.

5. The method of claim 1, wherein said interstitial fluid-transporting layer is transparent to said light.

6. The method of claim 1, wherein said interstitial fluid-transporting layer is a mesh.

7. The method of claim 1, wherein said interstitial fluid transporting layer comprises a surfactant.

8. The method of claim 1, wherein said interstitial fluid-transporting layer has an opening therein.

9. The method of claim 1, wherein said interstitial fluid-transporting layer and said overcoat layer are substantially coplanar.

10. The method of claim 1, wherein said interstitial fluid transporting layer has edges, said edges being embedded in said overcoat layer.

11. The method of claim 1, wherein said analyte-detecting layer detects analyte by means of an electrical measurement.

12. The method of claim 1, wherein said analyte-detecting layer detects analyte by means of an optical measurement.

13. The method of claim 1, wherein said source of light is a laser.

14. The method of claim 1, wherein said source of light is a pulsed high intensity white light.

15. The method of claim 1, wherein the amount of interstitial fluid collected is less than two microliters.

16. The method of claim 1, wherein the amount of interstitial fluid collected is less than one microliter.

17. Article for collecting and analyzing interstitial fluid to detect the presence of an analyte therein comprising:

a multiple-layer element comprising:
(1) a layer that is capable of being placed in contact with the skin of a patient;
(2) an overcoat layer that is coated over the skin-contacting layer;
(3) a layer, substantially coplanar with the overcoat layer, that is capable of transporting interstitial fluid by means of chemically aided wicking;
(4) a layer, overlying the interstitial fluid transporting layer, that is capable of being placed in contact with a meter, said layer having an opening therein through which light can be transmitted;
(5) a layer in communication with the interstitial fluid transporting layer, which layer is capable of detecting the presence of analyte or measuring the amount of analyte in the fluid.

18. The article of claim 17, wherein said skin-contacting layer has a target for light.

19. The article of claim 18, wherein said target comprises a dye or a pigment.

20. The article of claim 18, wherein said skin-contacting layer bears an adhesive on one major surface thereof.

21. The article of claim 17, wherein said interstitial fluid-transporting layer is transparent to light.

22. The article of claim 17, wherein said interstitial fluid-transporting layer is a mesh.

23. The article of claim 17, wherein said interstitial fluid transporting layer comprises a surfactant.

24. The article of claim 17, wherein said interstitial fluid-transporting layer has an opening therein.

25. The article of claim 17, wherein said interstitial fluid-transporting layer and said overcoat layer are substantially coplanar.

26. The article of claim 17, wherein said interstitial fluid-transporting layer has edges, said edges being embedded in said overcoat layer.

27. The article of claim 19, wherein said analyte-detecting layer detects analyte by means of an electrical measurement.

28. The article of claim 17, wherein said analyte-detecting layer detects analyte by means of an optical measurement.

29. The article of claim 18, wherein said light is provided by a laser.

30. The article of claim 18, wherein said light is provided by a pulsed high intensity white light.

31. The article of claim 17, wherein no more than two microliters of interstitial fluid are required for analyte determination.

32. The article of claim 17, wherein no more than one microliter of interstitial fluid is required for analyte determination.

* * * * *